United States Patent [19]

Walter

[11] Patent Number: 5,068,463
[45] Date of Patent: Nov. 26, 1991

[54] PROCESS FOR THE PREPARATION OF TETRABROMO-4,4'-ALKYLIDENEDIPHENOLS

[76] Inventor: Eberhard Walter, Schifferstrasse 88, D-6000 Frankfurt/Main 70, Fed. Rep. of Germany

[21] Appl. No.: 592,473

[22] Filed: Oct. 5, 1990

[30] Foreign Application Priority Data

Oct. 23, 1989 [DE] Fed. Rep. of Germany ....... 3935224

[51] Int. Cl.$^5$ .................. C07C 37/62; C07C 39/16
[52] U.S. Cl. ................................. 568/726; 568/722; 568/728; 568/730
[58] Field of Search .............. 568/722, 726, 728, 730

[56] References Cited

U.S. PATENT DOCUMENTS 3,929,907 12/1975 Janzon et al. .................. 568/726

FOREIGN PATENT DOCUMENTS 493458 3/1976 U.S.S.R. .............................. 568/726

Primary Examiner—Werren B. Lone
Attorney, Agent, or Firm—Cushman, Darby & Cushman

[57] ABSTRACT

A process for the production of tetrabromo-4,4'-alkylidenediphenols, especially tetrabromobisphenol A (TBBA), from the corresponding alkylidenediphenols by oxidative bromination with $Br_2$, $HBr_3$ or $HBr$ and aqueous hydrogen peroxide in the presence of an organic solvent. The process is characterized by washing the organic phase containing dissolved tetrabromo-4,4'-alkylidenediphenol with an aqueous alkali sulphite solution, preferably at 50° to 90° C. Through this washing treatment, the tetrabromo compound is obtained in higher purity; in addition, the mother liquor can be recycled without difficulty.

7 Claims, 1 Drawing Sheet

APHA number and saponifiable bromine content (ppm) of TBBA
(I) according to the invention- with sulphite wash
(II) prior art- without sulphite wash

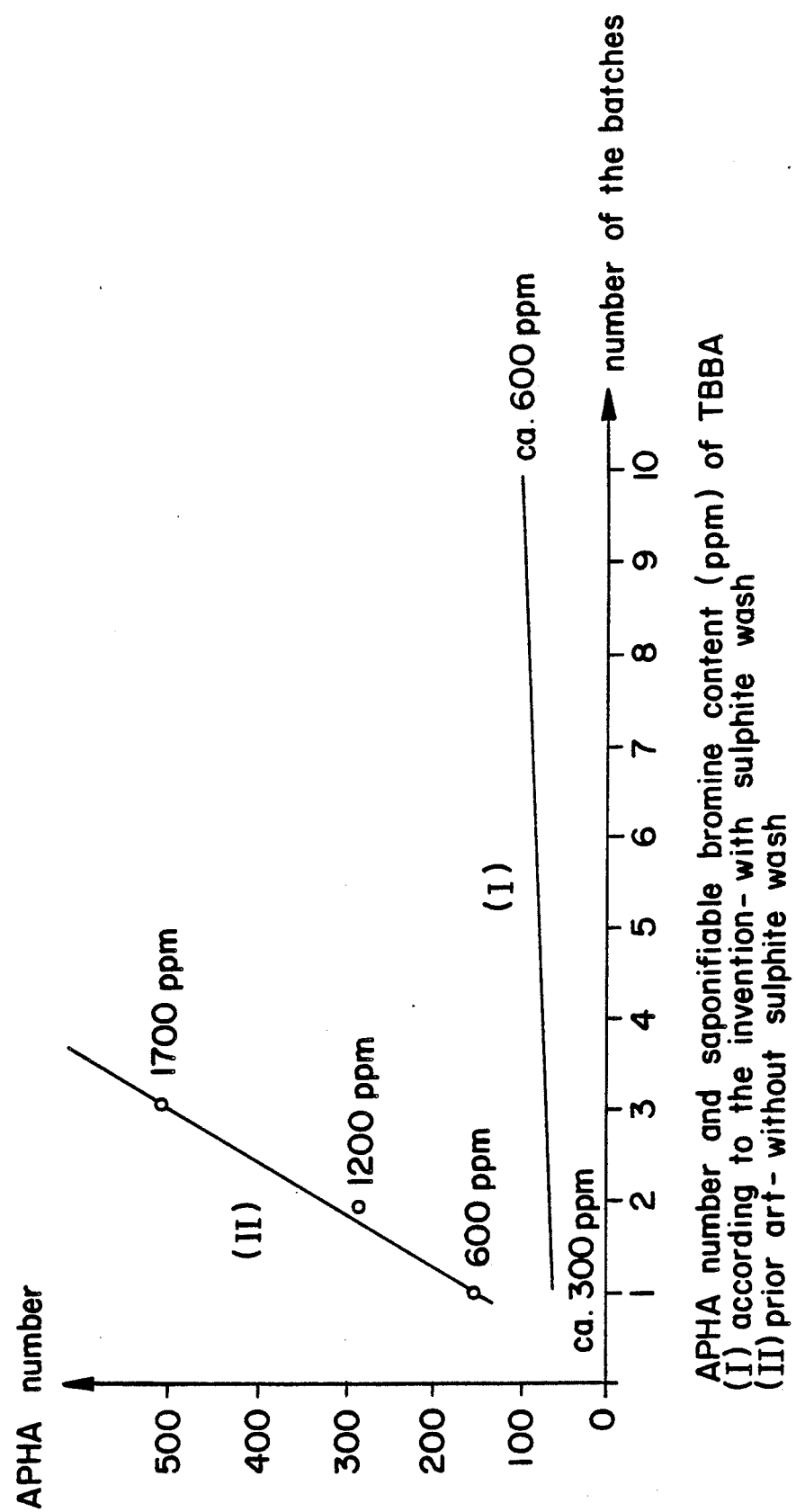

PROCESS FOR THE PREPARATION OF TETRABROMO-4,4'-ALKYLIDENEDIPHENOLS

The present invention relates to a process for the production of tetrabromo-4,4'-alkylidenediphenols, which are understood to include 4,4'-alkylidene-bis(2,6-dibromophenols). The invention relates especially to the synthesis of 4,4'-isopropylidene-bis(2,6-dibromophenol), which is also known as 2,2-bis(3,5-dibromo-4-hydroxyphenyl)propane, but usually as tetrabromobisphenol A or TBBA for short. The process of the invention is based on the bromination of alkylidenediphenols with bromine in the presence of hydrogen peroxide and is characterized by a wash stage. The process makes it possible to recycle the mother liquor and to produce tetrabromo-4,4'-alkylidenediphenols in high yield and high quality.

BACKGROUND OF THE INVENTION

Nuclear brominated phenolic compounds, such as tetrabromobisphenol A (TBBA) and tribromophenol, are used in plastics materials and synthetic resins as flameproofing agents. TBBA is particularly important for this purpose, since it can be incorporated reactively into polymer systems, for instance epoxy resins and polyesters, via the two phenolic hydroxyl groups. For this application, it is necessary to use high quality tetrabromo-4,4'-alkylidenediphenols; the products must be as free as possible from byproducts, have as low as possible a color number, and be essentially free from hydrolyzable bromine.

Commercial grades of TBBA sometimes have high APHA color values, so that their use, particularly in transparent products, leads to undesirable colorations. Other difficulties arise if the content of aliphatically combined bromine is high, because these substances can cause corrosion through the hydrolytic or thermal elimination of hydrobromic acid and reduce the electrical insulation values of synthetic resins flameproofed with such TBBA. In many cases the plastics processor is forced to purify standard grades himself or to use special grades, each of which leads to increased costs.

The bromination of 4,4'-alkylidenediphenols with bromine to the nuclear brominated tetrabromo-4,4'-alkylidenediphenols is well known. The hydrobromic acid liberated during the bromination can be oxidized to bromine and re-used. Sulphur trioxide and chlorine have been used for the reoxidation. However, their use leads to considerable environmental pollution because of the formation of sulphur dioxide or hydrogen chloride.

A simple and environmentally acceptable process, by which phenols and 4,4'-alkylidenediphenols are brominated in presence of hydrogen peroxide, has been described in the U.S. Pat. No. 3,929,907. In this process, which also is used in the present invention, the hydrobromic acid arising in the bromination is oxidized in situ by aqueous hydrogen peroxide solution to bromine, which is then available for further bromination. The peroxy-bromination of 4,4'-alkylidenediphenols, such as bisphenol A, takes place at 0° C. to 100° C. in the presence of an inert organic solvent which is not miscible with water but is suitable for the crystallization of the tetrabromo-4,4'-alkylidenediphenols. After the bromination, the reaction mixture is heated sufficiently to dissolve the suspended reaction product in the organic phase, and the aqueous phase can be separated; then the organic phase is cooled, causing the brominated product to crystallize following which the product can be isolated in known manner.

By multiple reuse of the mother liquor of the process of U.S. Pat. No. 3,929,907, the yield can indeed be increased, but it has been found that this reduced the quality of the tetrabromo-4,4'-alkylidenediphenol. This becomes particularly clear in the APHA color number and the saponifiable bromine content, which approximately doubles even after a single recycling of the mother liquor. In the previously known peroxybromination of bisphenol A to TBB carried out on the industrial scale using chlorobenzene as solvent, without mother liquor recycle, the TBBA has an APHA color number of about 150 and a saponifiable bromide content of about 600 ppm; this quality could only be maintained in subsequent batches if the mother liquor was first freed from quality-lowering substances by redistillation before being reused. A redistillation of the entire mother liquor is very expensive.

SUMMARY OF THE INVENTION

The object of the present invention is to improve the previously known process of peroxybromination for the production of tetrabromo-4,4'-alkylidenediphenols, especially of TBBA, from the corresponding 4,4'-alkylidenediphenols so that the quality-determining features of the brominated products remain largely constant, even with multiple recycling of the mother liquor. A further object of the present invention is to increase the quality of the product above the level previously reached by peroxybromination without reducing the yield and without appreciably increasing the total cost of the process.

These and other objects are achieved in a process for the production of tetrabromo-4,4'-alkylidenediphenols of high purity by bromination of the corresponding 4,4'-alkylidenediphenols with bromine or an aqueous HBr or $HBr_3$ solution. In the process, HBr which is charged and/or formed during the bromination, is oxidized to bromine by aqueous hydrogen peroxide in the presence of a water-immiscible organic solvent or solvent mixture. After completion of the reaction, the tetrabromo-4,4'-alkylidenediphenol, which has formed, is dissolved in the organic phase by raising the temperature of the reaction mixture. Then, the aqueous is separated from the organic phase is cooled, causing the tetrabromo-4,4'-alkylidenediphenol to crystallize, and the crystals are separated from the mother liquor. The process of the invention includes the steps of washing the organic liquid at least once prior to the crystallization step with an aqueous alkali sulphite solution and at least once with water and removing the aqueous phase after each wash the aqueous phase is removed.

In accordance with the exemplary embodiment of U.S. Pat. No. 3,929,907, bromine can first be added to a mixture of the 4,4'-alkylidenediphenol and the organic solvent, following which an aqueous hydrogen peroxide solution can be metered in. According to the invention, however, the reverse sequence is preferred, that is, there is a controlled metered addition of the bromine to a mixture of the 4,4'-alkylidenediphenol, generally present in suspension in the organic solvent and the aqueous hydrogen peroxide. It is preferable to limit the temperature during the bromine addition to 40° C., preferably 30° C.; owing to the large heat of reaction, cooling is needed to achieve this. In place of bromine, aqueous solutions of hydrobromic acid or concentrated solutions of bromine in hydrobromic acid (HBr$_3$) can also be used for the bromination.

The 4,4'-alkylidenediphenol, bromine and hydrogen peroxide are preferably charged in a molar ration 1:2–2.1:2–2.2. In the case of HBr-containing bromination systems, 1 to 1.1 mole hydrogen peroxide is used per mole of HBr and of Br$_2$.

It is, certainly, possible to use a larger excess of hydrogen peroxide, but this does not lead to perceptible advantages for the process and/or quality of the product. An excess of about 3% bromine and about 5% hydrogen peroxide is in general fully sufficient.

The alkylidene group of the 4,4'-alkylidenediphenols to be brominated can contain 1–8 carbon atoms. However, the alkylidene group should not contain a tertiary C-H bond. The isopropylidene group is preferred.

The process according to the invention includes an integrated wash with an aqueous alkali sulphite solution of the organic phase, which contains, dissolved, the tetrabromo-4,4'-alkylidenediphenol formed in the bromination. In order to achieve a good washing effect, the wash is carried out at elevated temperature, preferably at 50° to 90° C., especially at 70° to 90° C. At least one washing sequence is used, but it can also be repeated several times, after carrying out a phase separation at the end of each sequence. Among the alkali sulphites which may be used, sodium sulphite is preferred. The concentration of the alkali sulphite solution can range over the whole concentration range up to the saturation limit at the selected treatment temperature; in general, the concentration will be in the range from 1 to 20% by weight, especially 5 to 15% by weight.

According to a preferred embodiment, for the washing of a saturated solution of TBBA in chlorobenzene, 25 to 100 g Na$_2$SO$_3$ per kg TBBA are used in the form of an aqueous solution at 50° to 90° C. Preferably the solution contains 10 to 15% Na$_2$SO$_3$ by weight. In general one wash stage is sufficient. The washing treatment can be carried out in simple tubular reactors or in wash columns or other apparatus which ensures a sufficiently thorough mixing of the two phases and possibly maintenance of the desired treatment temperature, such as for instance mixer-settler units. Depending on the intensity of the washing treatment and the temperature at which it is carried out, a contact time in the range of 1 to 60 minutes is required. At the especially preferred treatment temperature in the range of 70° to 90° C., a contact time of 5 to 20 minutes is in general sufficient. The washing treatment of the organic phase with an aqueous alkali sulphite solution is followed by at least one re-wash with water, in which there also is selected a temperature at which the dissolved tetrabromo-4,4'-alkylidenediphenol still does not crystallize out. In order to limit the water expenses in the process, it is advantageous to reuse the wash water in a successive batch for the production of the aqueous alkali sulphite solution. The used washing solutions can be disposed of simply by oxidizing the sulphite to sulphate, for example with hydrogen peroxide, and filtering off the bromophenols then arising; alternatively the bromo-organic constituents can also be removed from the waste water after the oxidation by extraction with the organic solvent used in the bromination.

After the washing treatment according to the invention and the last phase separation, the organic phase is allowed to cool, and the desired tetrabromo-4,4'-alkylidenediphenol crystallizes out. The crystallization and separation of the crystals from the mother liquor are carried out according to the generally known methods and by using conventional solid-liquid separation devices.

The bromination is carried out in the presence of an organic solvent which is inert towards the reactants, but which allows the tetrabromo compound to be crystallized out. The solvent used accordingly show a definite concentration-temperature gradient for the tetrabromo compound. Especially advantageous in this respect is chlorobenzene; for this solvent, the saturation concentration of TBBA at 20° C. is 185 g/l, and at 90° C. is 805 g/l. Other solvents are those named in U.S. Pat. No. 3,929,907, such as for instance benzene, halogenated aliphatic hydrocarbons, and 2-ethylhexanol in combination with aliphatic hydrocarbons. Solvents with a boiling point in the range of about 80° to 200° C., especially about 80° to 150° C., are preferred. The phenol to be brominated can dissolve in the solvent completely or partially; but it can also be reacted as solid suspended in it, as is the case for the oxidative bromination of bisphenol A to TBBA in chlorobenzene.

By means of the wash steps with aqueous alkali sulfite solution according to the invention, it is surprisingly possible to recycle the greater part of the mother liquor into the process, after the crystallization and filtration, without distillation. It is sufficient each time to withdraw and distill only a small part, in general about 5 to 10% of the mother liquor; in doing this, the corresponding part of the solvent is recovered, and 2,4,6-tribromophenol, which is itself a flameproofing agent, can be recovered from the bottom of the distillation column. Besides the recyclability of the mother liquor, the quality of the tetrabromo-4,4'-alkylidenediphenol produced is improved with respect to the color number and the saponifiable bromine content, which could not have been foreseen. FIG. 1 shows the values found for the above-mentioned quality characteristics of TBBA produced according to the process of the invention, from the example of successive batches for the production of TBAA on a pilot plant scale. See Curve (I) which shows the results with the invention and Curve 2 which shows the results with the previously-known process. Batches according to (I) and (II) were oxidatively brominated and crystallized under the same conditions, and each time the whole mother liquor was recycled into the following batch. The superiority of the process according to the invention is obvious from FIG. 1.

By using the wash steps according to the invention with an aqueous sulphite solution, color-bearing byproducts, probably with quinonoid structure, are converted to colorless compounds, and byproducts with aliphatically combined bromine are partly hydrolyzed and partly discharged from the system with the wash phase. By the steps according to the invention, a TBBA of better quality is produced, the byproducts are made harmless and consequently the mother liquor may be recycled without difficulty.

DETAILED DESCRIPTION OF PREFERRED EMBODIMENTS

Example 1

Serial investigation on the production of TBBA from bisphenol A and bromine/H$_2$O$_2$ Chlorobenzene together with an aqueous solution of hydrogen peroxide and bisphenol A are charged to an enamelled stirred vessel. For the reaction, bromine is metered into the thoroughly mixed suspension. The heat of reaction is removed by brine cooling. The bromine addition is controlled so that a maximum temperature of 30° C. is not exceeded. The added bromine reacts rapidly. After the bromine addition, the suspension is heated to 80° C., and the TBBA which has formed goes into solution quantitatively. The aqueous phase is separated from the organic phase. The organic phase containing the dissolved TBBA is washed with intensive mixing at about 80° C., once with a 1 molar aqueous sodium sulphite solution—250 ml per mole TBBA—and twice with water; after each wash process, the aqueous phase is siphoned off. For the crystallization, the organic phase is slowly cooled to 20° C. The solid suspension formed is separated in a centrifuge. The moist product, containing 5–10% chlorobenzene, is dried in the usual way.

For each mole of bisphenol A, there are added 2.1 moles 50% by weight aqueous hydrogen peroxide, which had been acidified with 3% by weight of $H_2SO_4$, and 2.06 moles bromine; also for each mole of bisphenol A in the first batch, 800 ml chlorobenzene were added. The mother liquor was used in the subsequent batch without replacing the solvent losses, the amounts of the reactants in the subsequent batches being reduced in the same ratio.

The results of the 10 successive experiments can be seen in Table 1. The total yield of dry TBBA was 96.4% of theory, and the mother liquor after the 10th batch contained a further 124 g TBBA, corresponding to 1.6% of theory, as well as 100 g tribromophenol.

TABLE 1

| Experiment No. | Bisphenol A fed (g) | TBBA (dry) (g) | Mother liquor (ml) | APHA # of the TBBA*) | Saponifiable bromide content**) of the TBBA (ppm) |
|---|---|---|---|---|---|
| 1 | 570 | 1082 | 1935 | 10 | 300 |
| 2 | 428 | 1032 | 1760 | 10 | 300 |
| 3 | 377 | 886 | 1600 | 10 | 300 |
| 4 | 343 | 833 | 1500 | 30 | 360 |
| 5 | 321 | 755 | 1370 | 40 | 430 |
| 6 | 293 | 705 | 1270 | 40 | 480 |
| 7 | 272 | 643 | 1170 | 50 | 520 |
| 8 | 250 | 603 | 1060 | 50 | 520 |
| 9 | 227 | 528 | 1000 | 70 | 580 |
| 10 | 212 | 516 | 920 | 60 | 590 |

*)Determination according to DIN 53 409, by which 50 ml of, 50% by weight solution of TBAA in acetone is compared with [CoPtCl₆] standard solutions.
**)Determination by 1 hour's boiling of 100 g TBBA with a 10% by weight NaOH solution, neutralization, filtration off of the TBAA and washing, and determination of the bromine content.

Example 2

Serial investigation on the production of TBBA from bisphenol A and HBr/$H_2O_2$.

The process sequence corresponded to that of Example 1; however, oxidative bromination was carried out with concentrated aqueous HBr/$H_2O_2$ instead of with bromine/$H_2O_2$. The molar ratio was bisphenol A:HBr:$H_2O_2$ = 1:4.12:4.2. Further, in the first batch, the chlorobenzene (1000 ml) was presaturated with 225 g TBBA. In order to allow for the chlorobenzene discharged with the TBBA formed, 100 ml fresh chlorobenzene was added each time from the 2nd batch; in 10 successive experiments with complete recycle of the mother liquor, each time 1 mole bisphenol A was charged, reacted and washed according to the invention as in Example 1. The results are given in Table 2. The total yield of dry TBBA was 94.5% of theory, including TBBA from the saturation; there was a further 2.5% of theory in the mother liquor of the 10th batch.

TABLE 2

| | TBAA substance data | | | |
|---|---|---|---|---|
| Experiment no. | TBAA (dry) (g) | Mother liquor (ml) | Melting point (°C.) | APHA number |
| 1 | 603 | 1310 | 181–182 | 10 |
| 2 | 494 | 1300 | 180–182 | 20 |
| 3 | 513 | 1300 | 180–182 | 20 |
| 4 | 559 | 1280 | 180–182 | 20 |
| 5 | 497 | 1300 | 179–182 | 30 |
| 6 | 533 | 1260 | 179–182 | 20 |
| 7 | 470 | 1300 | 179–180 | 20 |
| 8 | 537 | 1290 | 178–181 | 20 |
| 9 | 590 | 1260 | 179–181 | 30 |
| 10 | 551 | 1220 | 179–181 | 30 |

What is claimed is:

1. In a process for the production of tetrabromo-4,4'-alkylidenediphenols of high purity which comprises brominating the corresponding 4,4'-alkylidenediphenols with bromine or an aqueous $HBr_3$ or HBr solution in the presence of a water-immiscible organic solvent or solvent mixture, while HBr is oxidized to bromine by aqueous hydrogen peroxide, dissolving the tetrabromo-4,4'-alkylidenediphenol formed in the reaction in the organic phase, after completion of the reaction, by raising the temperature of the reaction mixture, separating the aqueous phase from the organic phase, cooling the organic phase and thereby crystallizing the tetrabromo-4,4'-alkylidenediphenol and separating the crystals from the mother liquor;

the improvement which comprises washing the organic phase before the crystallization at least once with an aqueous alkali sulphite solution and at least once with water and removing the aqueous phase after each wash.

2. A process as set forth in claim 1 in which the organic phase is washed at 50°–90° C. with a 1–20% by weight aqueous sodium sulphite solution.

3. A process as set forth in claim 2 in which the organic phase is washed at 70°–90° C. with a 5–15% by weight aqueous sodium sulphite solution.

4. A process as set forth in claim 1 in which 4,4'-isopropylidenediphenol, bromine and hydrogen peroxide are used in the molar ratio 1:2–2.1:2–2.2.

5. A process as set forth in any one of claims 1–5 in which the tetrabromo-4,4'-alkylidenediphenol is tetrabromobisphenol A.

6. A method as set forth in claim 1 in which HBr is formed during the bromination and is oxidized to bromine by aqueous hydrogen peroxide.

7. A method as set forth in claim 1 in which HBr is added to the reaction mixture and is oxidized to bromine by aqueous hydrogen peroxide.

* * * * *